United States Patent
DiMauro

(10) Patent No.: US 8,852,209 B2
(45) Date of Patent: Oct. 7, 2014

(54) INSTRUMENT ADAPTOR FOR IMAGE GUIDED SURGERY

(75) Inventor: Thomas M. DiMauro, Raynham, MA (US)

(73) Assignee: DePuy Synthes Products, LLC, Raynham, MA (US)

(*) Notice: Subject to any disclaimer, the term of this patent is extended or adjusted under 35 U.S.C. 154(b) by 551 days.

(21) Appl. No.: 13/053,963

(22) Filed: Apr. 7, 2011

(65) Prior Publication Data

US 2012/0259172 A1 Oct. 11, 2012

(51) Int. Cl.
*A61B 19/00* (2006.01)

(52) U.S. Cl.
USPC .................................. 606/130; 600/407

(58) Field of Classification Search
CPC ........... A61B 19/54; A61B 19/26; A61B 1/00
USPC .......... 606/130, 131, 170, 108; 600/104, 417, 600/424, 429, 407, 427
See application file for complete search history.

(56) References Cited

U.S. PATENT DOCUMENTS

| | | |
|---|---|---|
| 5,769,861 A | 6/1998 | Vilsmeier |
| 5,771,760 A | 6/1998 | Tiede |
| 5,778,743 A | 7/1998 | Tiede |
| 5,848,680 A | 12/1998 | Rinner |
| 5,873,288 A | 2/1999 | Gauthier |
| 5,879,397 A | 3/1999 | Kalberer |
| 5,943,755 A | 8/1999 | Gauthier |
| 6,021,343 A | 2/2000 | Foley |
| 6,190,395 B1 | 2/2001 | Williams |
| 6,428,547 B1 | 8/2002 | Vilsmeier |
| 7,226,456 B2 | 6/2007 | O'Neil |
| 7,237,556 B2* | 7/2007 | Smothers et al. ............. 128/898 |
| 7,351,253 B2* | 4/2008 | DiMauro et al. ................ 607/88 |
| 8,083,727 B2* | 12/2011 | Kugler et al. ................ 604/509 |
| 2003/0149351 A1* | 8/2003 | Nowinski et al. ............. 600/407 |
| 2003/0181918 A1 | 9/2003 | Smothers et al. |
| 2007/0055232 A1 | 3/2007 | Colquhoun |
| 2010/0268067 A1 | 10/2010 | Razzaque et al. |

FOREIGN PATENT DOCUMENTS

WO WO 03071969 9/2003

* cited by examiner

*Primary Examiner* — Victor Nguyen

(57) ABSTRACT

The invention relates to an adaptor for tracking an instrument location during image guided surgery. The adaptor has a drive shaft, a proximal handle and a distal instrument tip. The drive shaft has a linear proximal portion, a curved mid-portion and a linear distal portion that is co-linear with the linear proximal portion. Three tracking elements (such as reflective balls) are placed on the sinusoidal portion. When the handle is rotated, the two linear portions remain fixed on the longitudinal axis, but the tracking elements on the sinusoidal portion travel in orbits about the longitudinal axis, thereby allowing a computer to track the location of the instrument tip.

12 Claims, 7 Drawing Sheets

INSTRUMENT ADAPTOR FOR IMAGE GUIDED SURGERY

BACKGROUND OF THE INVENTION

Computer-assisted, image-guided medical and surgical navigation systems are known and used to generate images in order to guide a surgeon during a medical procedure. See, for example, U.S. Pat. Nos. 5,769,861 & 6,428,547. Such systems frequently include a tracking array that is clamped to the instrument desired to be tracked.

U.S. Pat. No. 6,190,395 ("Williams") discloses an image guided surgery (IGS) instrument having a flexible clamping band used to attach the tracking array to the instrument tip.

U.S. Pat. No. 6,021,343 ("Foley") discloses a tool for use in image guided surgery comprising an annular guide member having a trackable array and a drive shaft for rotating an instrument such as a screwdriver while keeping the array stationary. Foley discloses an IGS instrument comprising a drive shaft, a proximal handle, a distal instrument tip, a guide that rotates around the driver shaft, and a tracking array that is mounted on the guide. In each embodiment disclosed in Foley, the drive shaft is received within an annulus of the guide member. That is, the annulus of the guide member surrounds the drive shaft, thereby allowing the array to rotate fully around the drive shaft. Further, Foley discloses attaching the instrument to the drive shaft by a simple male-female socket arrangement, in particular, a ball-and-detent mechanism. The ball and detent feature of this socket produces considerable error in tracking because the attachment occurs on one side of the connection and so is not substantially radially uniform.

PCT Published Patent Application No. WO03-071969 ("DePuy International") discloses a surgical instrument system includes a tool including an elongate shaft which defines the tool axis. The shaft bears a plurality of marker rings arranged in a predetermined pattern on the surface of the shaft so that they extend around the shaft axis, the marker rings identifying the tool. The system includes a device for receiving signals from the rings, and a data processor for analysing the signal from the rings and generating information relating to the identity of the tool.

SUMMARY OF THE INVENTION

The present invention relates to an adaptor for tracking an instrument's location during image guided surgery. The adaptor has a drive shaft, a proximal handle and a distal instrument tip. The drive shaft typically has a linear proximal portion, a curved mid-portion and a linear distal portion that is co-linear with the linear proximal portion. Three tracking elements (such as reflective spheres) are mounted on the shaft to form a triangle. Preferably, at least two of the tracking elements are mounted on the curved portion of the shaft. When the handle is manually rotated about the longitudinal axis, the two linear portions of the shaft remain fixed on the longitudinal axis, but the tracking element(s) on the curved portion of the shaft travel in orbits about the longitudinal axis, thereby allowing a computer to accurately track the location of the instrument tip Therefore, in accordance with the present invention, there is provided an instrument adaptor for use in image guided surgery, comprising:
   a) a proximal end portion forming a handle,
   b) a distal end portion comprising a connection for connecting to an instrument tip, and
   c) an intermediate portion therebetween having a shaft and at least three tracking elements thereon,
   wherein the proximal and distal end portions define a longitudinal axis, and
   wherein the shaft comprises a curved portion that deviates from the longitudinal axis.

DETAILED DESCRIPTION OF THE INVENTION

Figure 1A:
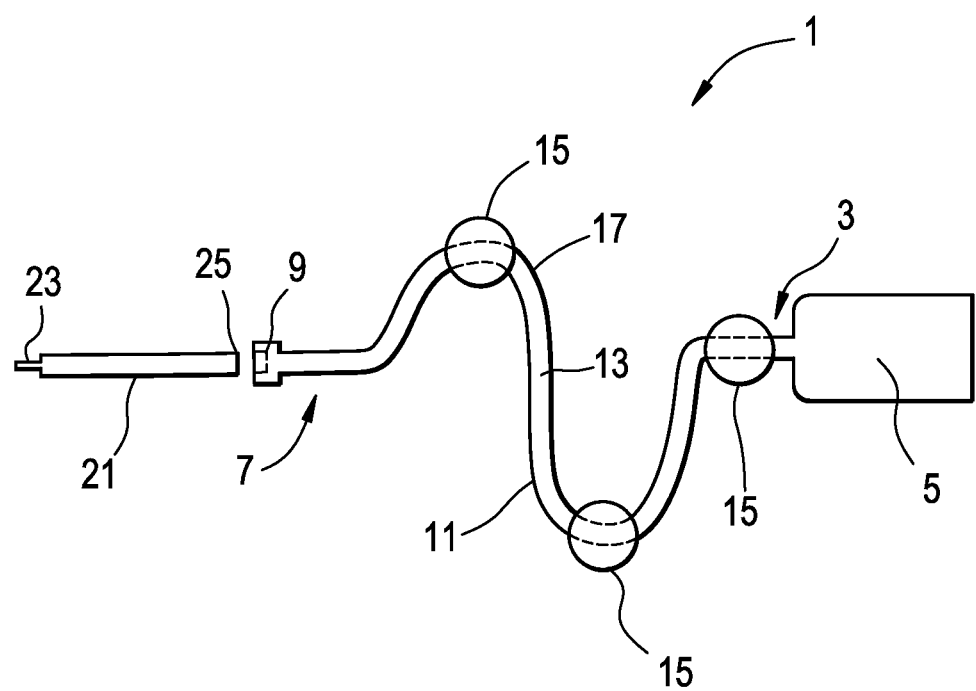
FIGS. 1A and 1B respectively disclose side views of embodiments of the IGS instrument and adaptor of the present invention.
Figure 1B:
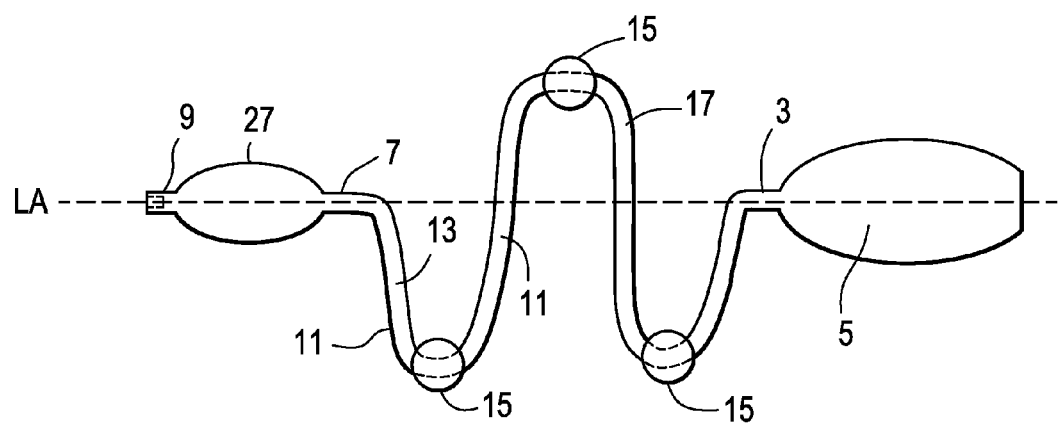

Now referring to FIGS. 1A and 1B, there is provided an instrument comprising:
   i) an instrument adaptor 1 for use in image guided surgery, comprising:
      a) a proximal end portion 3 forming a handle 5,
      b) a distal end portion 7 comprising a connection 9 for connecting to an instrument tip, and
      c) an intermediate portion 11 therebetween having a shaft 13 and at least three tracking elements 15 thereon,
      wherein the proximal and distal end portions define a longitudinal axis (LA), and
      wherein the shaft comprises a curved portion 17 that deviates from the longitudinal axis, and
   ii) the instrument tip 21 having a distal working end portion 23 and a proximal connection portion 25,
   wherein the proximal connection portion of the instrument tip is attached to the connection of the adaptor.

Now referring to FIG. 1B, there is provided an instrument substantially similar to that of FIG. 1A, but wherein each of the tracking elements is placed off the longitudinal axis LA. In addition, this instrument also includes a second handle 27 disposed on a distal portion 7 of the adaptor.

Preferably, the tools of the present invention are used in conjunction with a computer-assisted image-guided surgery system having i) a digitizer for tracking the position of the instrument in three-dimensional space, and ii) a display providing an indication of the position of the instrument with respect to images of a body part taken preoperatively. Preferably, the computer tracks the trajectory of the tool and the depth of the instrument inserted into the body part. In some embodiments, the computer-assisted image guided surgery system is that disclosed in U.S. Pat. Nos. 5,769,861 & 6,428,547, the specifications of which are incorporated by reference in their entireties.

The adaptor of the present invention generally comprises four portions: a proximal handle, an intermediate portion including a curved shaft, a distal connection for connecting to an instrument tip a plurality of tracking elements disposed on adaptor. Each of these portions will now be more fully discussed.

The function of the intermediate drive shaft component of the present invention is to transmit torque from the drive handle to the instrument. Preferably, the drive shaft is fixed axially and rotationally with respect to the drive handle and the instrument tip. In some embodiments, the drive shaft has a sinusoidal shape. In preferred embodiments thereof, the curved portion of the drive shaft comprises substantially one full period of a sinusoidal shape. In other embodiments, the drive shaft has a helical shape. In preferred embodiments thereof, the curved portion of the drive shaft comprises substantially one full period of a helical or sinusoidal shape.

The drive shaft also preferably has at least three tracking elements mounted thereon. Preferably, each of these tracking elements substantially fully envelops the circumference of the drive shaft upon which it is mounted so that each element can be continuously detected by the computer tracker during a full revolution of the shaft. The tracking elements of the present invention are axially fixed with respect to each of the power train components (i.e., the drive handle, the drive shaft and the instrument tip connection). These tracking elements generate a signal representing the trajectory of the tool and the depth of the instrument tip. Preferably, the tracking elements are passive, and more preferably comprise reflective surfaces. However, other tracking elements are known in the art capable of being tracked by a corresponding sensor array are within the scope of the present invention. For the purposes of illustration, and not limitation, the tracking elements may generate signals actively such as with acoustic, magnetic, electromagnetic, radiologic and micropulsed systems, and emitters such as LEDs.

Preferably, the plurality of trackers are arranged upon the shaft so as to form a triangle. In such a configuration, the tracker can more accurately perform triangulation and thereby determine the location of the instrument tip. Preferably, at least two of the tracking elements are disposed off of the longitudinal axis. In some embodiments, all three of the tracking elements are disposed off of the longitudinal axis. More preferably, first and second tracking elements are disposed on opposite sides of the longitudinal axis.

In some embodiments, the triangle is substantially defined by three points on the axially curved shaft.

In some embodiments, the tracking elements are attached to the shaft in a manner so that they may be easily removed. In this way, the adaptor is more amenable to easy cleaning Therefore, in accordance with the present invention, there is provided an instrument adaptor for use in image guided surgery, comprising:
 a) a proximal end portion forming a handle,
 b) a distal end portion comprising a connection for connecting to an instrument tip, and
 c) an intermediate portion therebetween having a shaft and at least three tracking elements thereon,
wherein the proximal and distal end portions define a longitudinal axis, and
wherein the tracking elements are removable.

In some embodiments, these tracking elements are intended to be disposable.

Figure 2A:
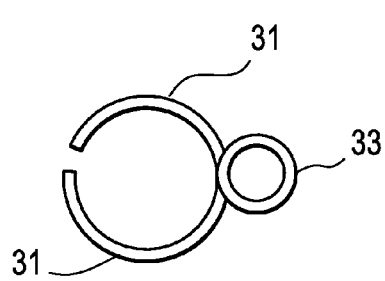
FIGS. 2A and 2B disclose a removable tracking element of the present invention having a clothespin-like function.
Figure 2B:
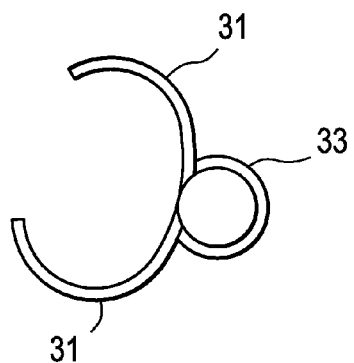

In some preferred embodiments, each tracking element comprises a clip that attaches to the shaft. Representative clips are shown in FIGS. 2A-2B. In these FIGS., the tracking element has a clothespin shape, with two opposed jaws 31 attached to a central spring element 33. In use, the jaws are opened, and the clip is placed upon the shaft at a predetermined location (which may be designated by a depression in the shaft having a length of the jaws). Once in the predetermined location, the jaws are closed to secure the tracking element to the shaft.

Figure 3:
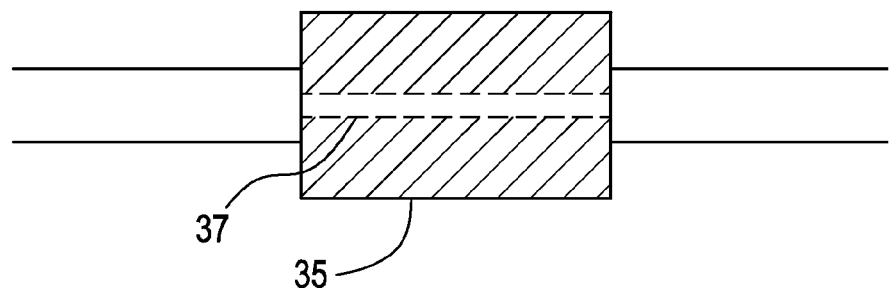
FIG. 3 discloses a removable tracking element of the present invention having a coil shape.
Figure 4A:
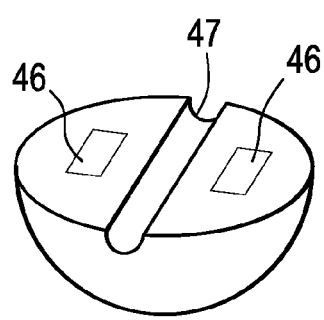
FIGS. 4A-4C disclose a two-piece, removable tracking element of the present invention having a central bore and an attachment means.
Figure 4B:
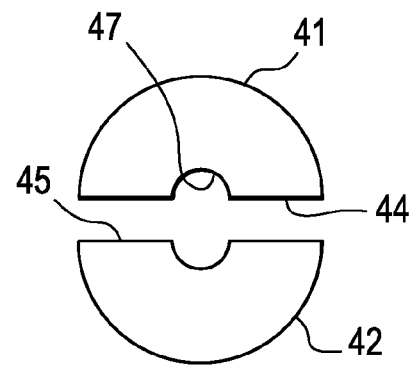
Figure 4C:
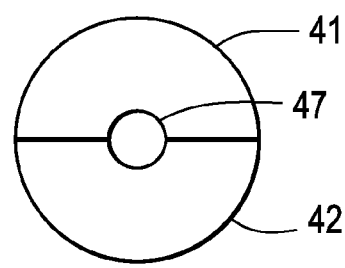
Figure 4D:
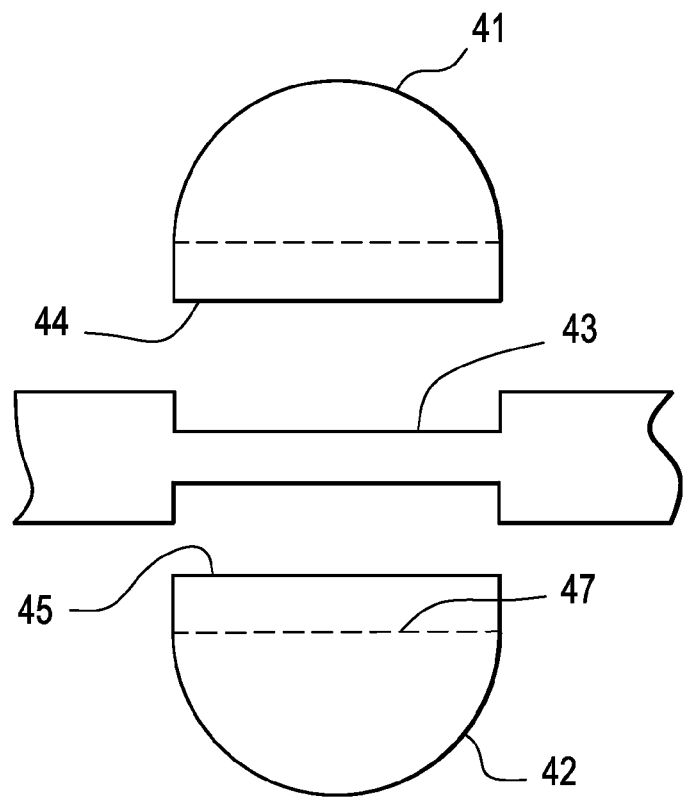
FIG. 4D discloses the tracking element of FIG. 4A disposed about a depression in the shaft of the handle of the present invention.

In some embodiments, as in FIG. 3, each tracking element is a coil 35 that is sufficiently flexible that it can be wound around a predetermined depressed region 37 in the shaft.

In some embodiments, and now referring to FIGS. 4A-4D, each tracking element comprises a pair of matching hemispheres 41,42 or hemicylinders. These shapes are desirable because they provide a substantially homogeneous surface for recognition by the tracker, thereby improving tracker accuracy. The hemispheres are particularly preferred because (when combined) they always provide a surface that is normal to the tracker. In use, the separated hemispheres are placed on opposite sides of a predetermined depression in the shaft, with their flat faces 44,45 facing each other (as in FIG. 4B). The two hemispheres are then brought together so that the semicylindrical depressions 47 in their flat faces enclose the recessed shaft region 43 therebetween. The flat faces of the hemispheres may preferably include means for removably attaching the hemispheres. The removable attachment means 46 may include hook-and-loop fasteners, magnets or pin-and-groove attachments.

Figure 5:
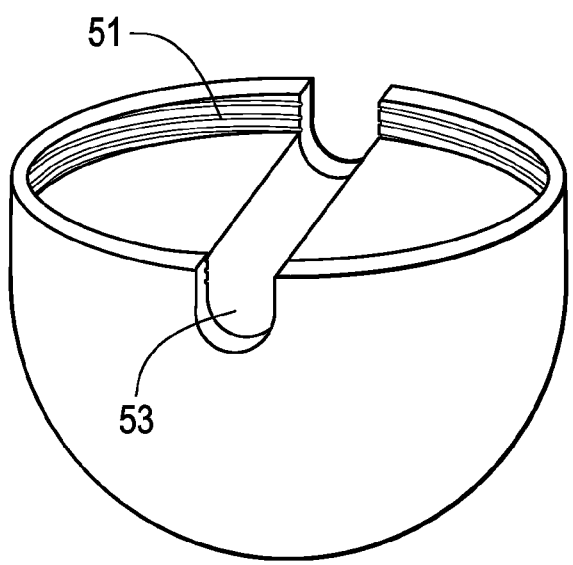
FIG. 5 disclose one half of a two-piece, removable tracking element of the present invention having a central bore and a threaded attachment means.

In some embodiments, the hemispheres have matching threaded features 51 extending from their flat faces. One such threaded feature is shown in FIG. 5. In use, the groove 53 of a first hemisphere is placed in contact with the depression on the shaft so that the shaft is fully received in the groove (i.e., the shaft does not extend past the flat face of the hemisphere), and the second hemisphere is then threaded onto the first hemisphere.

Figure 6A:
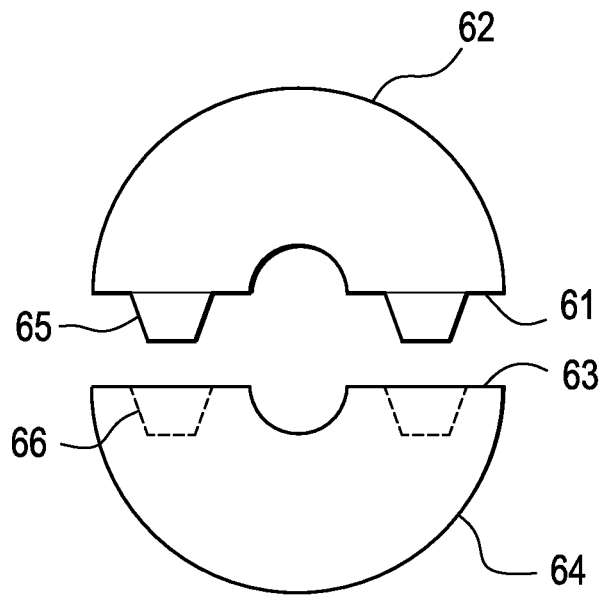
FIGS. 6A-6B each disclose a removable tracking element of the present invention having a central bore and a frustoconical attachment means.
Figure 6B:
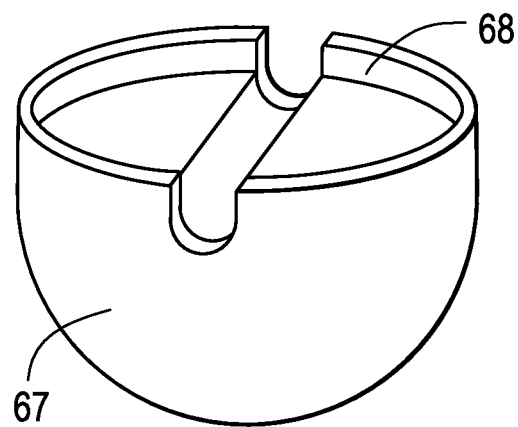

In some embodiments, as in FIGS. 6A and 6B, the flat faces 61,63 of the hemispheres 62,64 have mating frustoconical shapes 65,66 extending therefrom or therein. When the frustoconical shapes have an angle of between about 10 degrees and 25 degrees (and preferably about 18 degrees), they attach firmly to each other via a taper lock but are nonetheless able to be manually pulled apart. See, for example, U.S. Pat. No. 5,879,397, the specification of which is incorporated by reference in its entirety. In other embodiments, as in FIG. 6B, the hemispheres 67 have a frustoconcial rim 68 that provides the desired removable taper-locking.

Figure 7A:
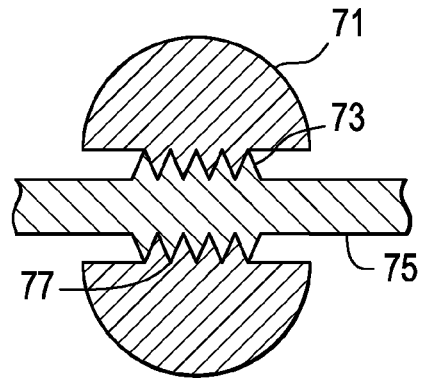
FIGS. 7A-7C disclose integral removable tracking elements of the present invention disposed about a threaded portion of the shaft, wherein each tracking element has a threaded central bore.
Figure 7B:
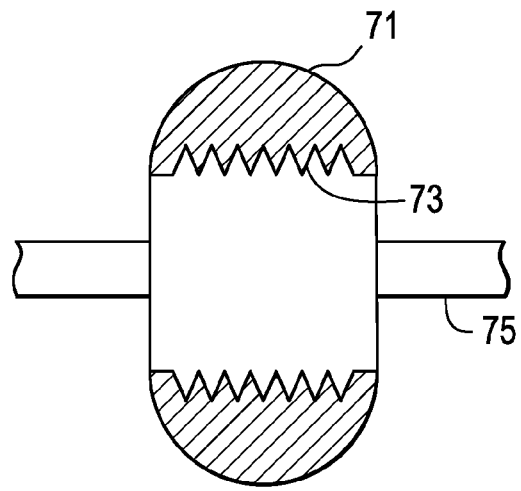
Figure 7C:
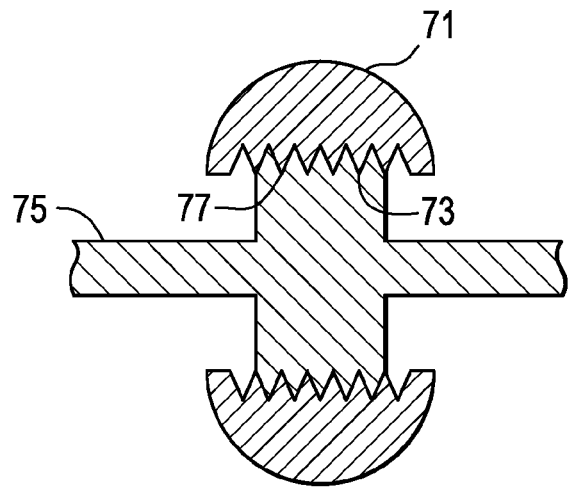

In some embodiments, as in FIGS. 7A-7C, the tracking elements 71 are integral spheres or cylinders having a single threaded bore 73 therein. FIG. 7A is cross-section of an embodiment wherein the tracking element is a sphere. FIG. 7B is a side view of an embodiment wherein the tracking element is a sphere. FIG. 7C is cross-section of an embodiment wherein the tracking element is a toroid.

The spheres are mounted on the shaft 75 upon at least three predetermined threaded risers 77 that extend radially from the shaft and mate with the threaded bores. This embodiment is advantageous because the spherical surface has no interruptions therein that could degrade the accuracy of the tracking In some embodiments, the middle riser has a height greater than the heights of the lateral risers. In some embodiments, the spheres having threaded bores are passed over a shaft having a helical shape.

Figure 8A:
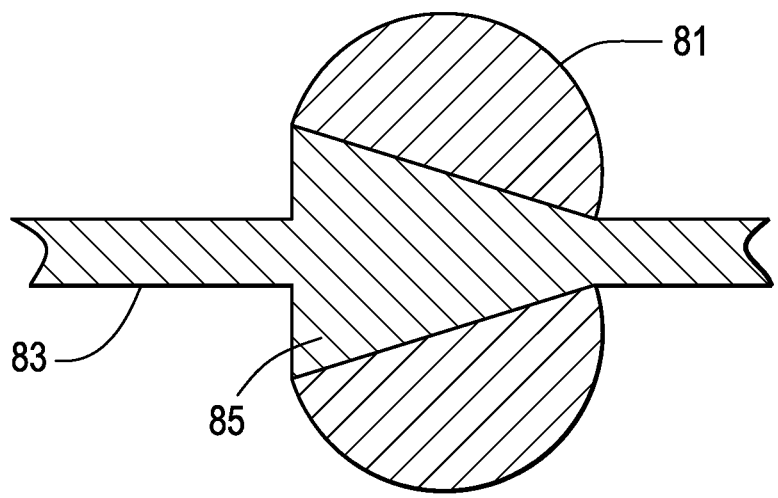
FIG. 8A discloses a cross-section of an integral removable tracking element of the present invention disposed about a frustoconical portion of the shaft.
Figure 8B:
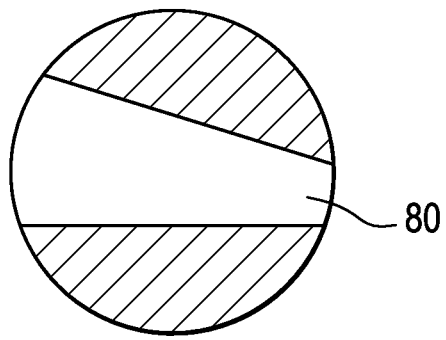
FIG. 8B discloses a cross-section of a spherical tracking element having a frustoconical bore.

In a related embodiment, and now referring to FIGS. 8A and 8B, each sphere 81 is mounted on the shaft 83 upon a predetermined frustoconcial riser 85 that extends radially from the shaft and mates with a frustoconical bore 80 of the sphere. In some embodiments, the middle riser has a height greater than the heights of the lateral risers.

The instrument tip is located at the distal end of the tool and attaches to the adaptor at the connection. When rotated, the instrument tip is able to work upon an implant or body part. Preferably, the instrument tip rotates in unison with the handle and shaft. Preferably, the instrument tip is axially fixed with respect to the handle and shaft. In some embodiments, the instrument is selected from the group consisting of a screwdriver, an awl, a tap, and a body having a shaped end for mating with a workpiece to be rotated.

The drive handle allows the surgeon to use manual force to impart rotary motion to the drive shaft and instrument tip. In some embodiments, the drive handle comprises a ratchet mechanism. In preferred embodiments, the ratchet mechanisms disclosed in U.S. Pat. Nos. 5,943,755; 5,873,288; 5,848,680; 5,778,743 and 5,771,760 are incorporated by reference in their entireties, are used.

In some embodiments, the tool may further comprise a guide handle 27, as shown in FIG. 1B. The purpose of the guide handle is to provide the user with a grippable surface for the non-dominant hand that allows the user to steady the tool while the drive handle is rotated. Preferably, the guide handle has radially extending finger grips (not shown). In some embodiments, the guide handle is attached to substantially an entire circumference of a distal portion of the shaft.

In preferred embodiments, the proximal end of the instrument tip is coupled to the distal end of the drive shaft by a connection, or "coupling means". Preferably, the coupling means provides a self-centered connection of the proximal end of the instrument to the distal end of the drive shaft. In some embodiments, the self-centering coupling means comprises a collet, as described in U.S. Pat. No. 7,226,456, the specification of which is incorporated by reference in its entirety. The collet provides the user with a quick connect/ disconnect option by simple hand twisting. The self-centering feature of the collet also provides a more accurate attachment of the instrument to the drive shaft than the ball-and-detent socket disclosed in the Foley patent. In some embodiments, the coupling means comprises a collet, a collet chuck and a collet nut.

Preferably, the instrument is inserted through the collet and into the collet chuck. In some embodiments, the transverse cross-section of the distal end of the collet chuck recess has a non-circular shape, such as a D-shaped drive feature. This feature provides enhanced torque transmission. In other embodiments, the coupling means may be a Hudson connection.

The function of the tool of the present invention is to help the surgeon track the trajectory of a surgical instrument placed within the body, thereby enhancing the access and accuracy of the spinal surgery procedure. Preferably, the selected instrument can mark, puncture, probe, tap, screw or guide the placement of an implant. Instruments are attached to the tool of the present invention by placing the proximal end of the instrument into the centering distal coupling means and preferably piloting the proximal end into the recessed 'D' feature of the collet chuck for increased torque. Rotation of the collet nut component of the coupling means centers and secures the instrument. The ratchet mechanism is then adjusted to select rotation options such as non-rotation, right hand drive and left handed drive.

When used with image guided surgery, the tool of the present invention is registered with an image guided surgery system to determine the trajectory and position of the instrument relative to the tracking array. This trajectory can be determined with preoperative CT or other imaging data to provide an operative display of instrument with bony tissue.

A preferred method with rotary drive instruments (tap or screw) comprises the steps of placing the surgeon's dominant hand on the proximal drive handle and the surgeon's non-dominant hand on the guide handle. Rotation is applied to the drive handle with dominant hand while non-dominant hand stabilizes the drive shaft. As rotation is imparted in the handle, the drive shaft rotates and torque is transferred through the drive mechanism to the instrument tip.

Typically, the components of the present invention can be made out of any material commonly used in medical instruments. Typically, the adaptor can be made out of a biocompatible metal, such as titanium alloy, cobalt-chrome and stainless steel. In some embodiments, the metal has a stiffness of at least 150 GPa (such as stainless steel and cobalt-chrome), so that any flexing of the shaft that may occur during use is minimized. If the device is designed to be reusable, it is preferred that all the components be made of stainless steel. If the device is designed to be disposable, it is preferred that some of the components (such as the handle) be made of plastic. Preferably, at least one component is sterilized. More preferably, each component of the adaptor is sterilized.

In some embodiments, the body part upon which the tool of the present invention works is hard tissue. In preferred embodiments, the hard tissue comprises bone. In more preferred embodiments, the body part is a human vertebra. In more preferred embodiments, the tool works upon the posterior portion of the vertebra.

Because the tracking elements are typically directly attached to a component of the drive train (e.g., the shaft), the tracking elements are thought to be spatially closer to the components of the drive train than were tracking elements in the prior art. This beneficially reduces the overall size of the instrument. Thus, in some embodiments, a first tracking element is located closer to the handle than to at least one other tracking element. Preferably, the first tracking element is located closer to the handle than to at least two other tracking elements. In some embodiments, a first tracking element is located closer to the connection than to at least one other tracking element. Preferably, the first tracking element is located closer to the connection than to at least two other tracking elements. In some embodiments, a first tracking element is located closer to the longitudinal axis than to at least one other tracking element. Preferably, the first tracking element is located closer to the longitudinal axis than to at least two other tracking elements.

I claim:

1. An instrument adaptor for use in image guided surgery, comprising:
   a) a proximal end portion forming a handle,
   b) a distal end portion comprising a connection for connecting to an instrument tip, and
   c) an intermediate portion therebetween having a shaft and at least three tracking elements thereon,
   wherein the proximal and distal end portions comprise substantially linear portions that define a longitudinal axis, and
   wherein the shaft comprises a curved portion that deviates from the longitudinal axis, wherein each tracking element substantially envelops a respective circumference of the shaft; and wherein at least two separate portions of the shaft deviate from the longitudinal axis.

2. The adaptor of claim 1 wherein each tracking element is selected from the group consisting of an emitter and a reflector.

3. The adaptor of claim 1 having an instrument tip connected to the connection.

4. The adaptor of claim 1 wherein the shaft comprises a helical portion.

5. The adaptor of claim 1 wherein the shaft comprises a sinusoidal portion.

6. The adaptor of claim 1 wherein at least two of the tracking elements are located off the longitudinal axis.

7. The adaptor of claim 1 wherein the shaft comprises a metal.

8. The adaptor of claim 1 wherein the shaft comprises a metal having a stiffness of at least 150 GPa.

9. The adaptor of claim 1 wherein the shaft comprises a metal selected from the group consisting of cobalt-chrome and stainless steel.

10. The adaptor of claim 1 wherein the tracking elements define a triangle.

11. The adaptor of claim 1 wherein each of the tracking elements are located upon the curved portion of the shaft.

12. The adaptor of claim 1 wherein the tracking elements are removable.

\* \* \* \* \*